(12) United States Patent
Fang et al.

(10) Patent No.: US 11,612,353 B2
(45) Date of Patent: Mar. 28, 2023

(54) EFFICACY AND/OR THERAPEUTIC PARAMETER RECOMMENDATION USING INDIVIDUAL PATIENT DATA AND THERAPEUTIC BRAIN NETWORK MAPS

(71) Applicant: LVIS Corporation, Palo Alto, CA (US)

(72) Inventors: Zhongnan Fang, Santa Clara, CA (US); Jin Hyung Lee, Palo Alto, CA (US)

(73) Assignee: LVIS Corporation, Palo Alto, CA (US)

( * ) Notice: Subject to any disclaimer, the term of this patent is extended or adjusted under 35 U.S.C. 154(b) by 415 days.

(21) Appl. No.: 16/762,905

(22) PCT Filed: Nov. 9, 2018

(86) PCT No.: PCT/US2018/060186
§ 371 (c)(1),
(2) Date: May 8, 2020

(87) PCT Pub. No.: WO2019/094836
PCT Pub. Date: May 16, 2019

(65) Prior Publication Data
US 2021/0169411 A1    Jun. 10, 2021

Related U.S. Application Data

(60) Provisional application No. 62/584,669, filed on Nov. 10, 2017.

(51) Int. Cl.
*G01R 33/48* (2006.01)
*G16H 10/60* (2018.01)
(Continued)

(52) U.S. Cl.
CPC .......... *A61B 5/4848* (2013.01); *A61B 5/0035* (2013.01); *A61B 5/0036* (2018.08);
(Continued)

(58) Field of Classification Search
CPC ........ G16H 50/20; G16H 20/30; G16H 20/40; A61B 6/037; G01R 33/4806;
(Continued)

(56) References Cited

U.S. PATENT DOCUMENTS 6,549,804 B1    4/2003   Osorio et al.
6,678,548 B1    1/2004   Echauz et al.
(Continued)

FOREIGN PATENT DOCUMENTS

CN    106909784 A    6/2017
JP    2002502270 A    1/2002
(Continued)

OTHER PUBLICATIONS

"Epilepsy Society: A closer look at EEG (Year 2022)".
(Continued)

*Primary Examiner* — Idowu O Osifade
(74) *Attorney, Agent, or Firm* — Dorsey & Whitney LLP

(57) ABSTRACT

Examples described herein may predict therapy efficacy and/or therapeutic parameters using a comparison of individual patient status data and brain network response maps for the therapy. For example, VNS parameters may be predicted using a comparison of patient EEG data and brain network response maps of VNS therapy at various parameters.

23 Claims, 6 Drawing Sheets

(51) Int. Cl.

| | |
|---|---|
| G16H 50/20 | (2018.01) |
| A61B 5/00 | (2006.01) |
| G16H 20/70 | (2018.01) |
| G06N 3/08 | (2023.01) |
| A61B 5/245 | (2021.01) |
| A61B 5/369 | (2021.01) |
| A61B 5/372 | (2021.01) |
| A61B 5/055 | (2006.01) |
| A61B 6/00 | (2006.01) |
| G06N 3/04 | (2023.01) |
| A61B 6/03 | (2006.01) |

(52) U.S. Cl.
CPC .............. *A61B 5/055* (2013.01); *A61B 5/245* (2021.01); *A61B 5/369* (2021.01); *A61B 5/372* (2021.01); *A61B 5/4094* (2013.01); *A61B 5/7267* (2013.01); *A61B 5/7275* (2013.01); *A61B 6/5247* (2013.01); *G01R 33/4808* (2013.01); *G06N 3/04* (2013.01); *G06N 3/08* (2013.01); *G16H 10/60* (2018.01); *G16H 20/70* (2018.01); *G16H 50/20* (2018.01); *A61B 6/037* (2013.01); *G01R 33/4806* (2013.01)

(58) Field of Classification Search
CPC ............... G06N 3/0454; G06N 3/0481; A61N 1/36064; A61N 1/36082
See application file for complete search history.

(56) References Cited

U.S. PATENT DOCUMENTS

| | | | |
|---|---|---|---|
| 2009/0306534 A1 | 12/2009 | Pizzagalli | |
| 2011/0119212 A1 | 5/2011 | De et al. | |
| 2011/0218950 A1 | 9/2011 | Mirowski et al. | |
| 2014/0128762 A1 | 5/2014 | Han et al. | |
| 2014/0243714 A1 | 8/2014 | Ward et al. | |
| 2015/0164431 A1 | 6/2015 | Terry et al. | |
| 2016/0019693 A1 | 1/2016 | Silbersweig et al. | |
| 2016/0300352 A1 | 10/2016 | Raj | |
| 2016/0375248 A1 | 12/2016 | Carcieri et al. | |
| 2017/0246481 A1* | 8/2017 | Mishelevich | A61N 2/006 |
| 2018/0140203 A1 | 5/2018 | Wang et al. | |
| 2018/0368720 A1 | 12/2018 | Lee et al. | |
| 2019/0142338 A1 | 5/2019 | Fang et al. | |
| 2021/0241908 A1 | 8/2021 | Ciupa et al. | |
| 2021/0282697 A1* | 9/2021 | Lee | A61B 5/4094 |
| 2022/0211319 A1* | 7/2022 | Harper | A61B 5/4094 |
| 2022/0257139 A1* | 8/2022 | Narayan | A61B 5/08 |

FOREIGN PATENT DOCUMENTS

| | | |
|---|---|---|
| WO | 2017040538 A1 | 3/2017 |
| WO | 2019094836 A1 | 5/2019 |

OTHER PUBLICATIONS

Hosseini, et al., "Deep Learning with Edge Compyting for Localization of Epileptogenicity using Multimodal rs-fMRI and EEG Big Data", IEEE International Conference on Autonomic Computing, 2017.
International Search Report and Written Opinion dated Jan. 22, 2019 for PCT Application No. PCT/US2018/060186.
International Preliminary Report on Patentability and Written Opinion for Application No. PCT/US2018/060186, dated May 12, 2020.
"Extended European Search Report for EP 18876659.6, dated Jul. 14, 2021".
Rosenberg, Ohansen Alexander, et al., "Epileptiform spike detection via convolutional neural networks", 2016 IEEE International Conference on Acoustics, Speech and Signal Processing (ICASSP), IEEE, Mar. 20, 2016, 754-758.
"Translation of Notice of Reasons for Refusal for Japanese Patent Appl. No. 2020-525846, dated Sep. 27, 2022".
"Office Action and Translation for CN Appl. No. 201880078009.0, dated Dec. 21, 2022".

* cited by examiner

EFFICACY AND/OR THERAPEUTIC PARAMETER RECOMMENDATION USING INDIVIDUAL PATIENT DATA AND THERAPEUTIC BRAIN NETWORK MAPS

CROSS-REFERENCE TO RELATED APPLICATION(S)

This application is a 35 U.S.C. 371 National Stage Application of PCT Application No. PCT/US2018/060186, filed Nov. 9, 2018, which claims the benefit under 35 U.S.C. 119 of the earlier filing date of U.S. Provisional Application No. 62/584,669 filed Nov. 10, 2017, the entire contents of which are hereby incorporated by reference, in their entirety, for any purposes.

TECHNICAL FIELD

Examples described herein relate generally to neural therapy, and examples of predicting the efficacy and/or parameters of treatments, such as neurostimulation treatment, are described.

BACKGROUND

Neurostimulation is an emerging promising therapy for neurological diseases including epilepsy, depression, Parkinson's disease, and Alzheimer's disease. However, currently there is no method to predict the efficacy of the therapy before implantation. In addition, because neurological diseases vary among individual patients (e.g. abnormal brain regions that cause seizure vary between epilepsy patients), repeated neurostimulation parameter adjustments are needed for each individual patient to identify his/her most effective stimulation setting. This long tedious parameter adjustment process has largely increased the medical care cost and causes frustration for both physician and patients. It has also reduced the overall efficacy of the neurostimulation therapy because many negative cases are results of early termination of the parameter adjustment.

SUMMARY

Examples of methods are described herein. An example method includes obtaining individual patient data of a neural status of a patient, obtaining a therapeutic brain network response map of a treatment, and predicting an efficacy of the treatment for the patient based on a comparison of the data of the neural status and the brain network response map.

In some examples, predicting the efficacy of the treatment may include providing the individual patient data and the therapeutic brain network response map as inputs to a statistical prediction model for the treatment, and predicting the efficacy of the treatment using the statistical prediction model.

In some examples, the statistical prediction model may include feature extraction techniques configured to extract features from the individual patient data regarding neural status and the brain network response map.

In some examples, the features may include an overlap area between the individual patient data and the brain network response map.

In some examples, the statistical prediction model may include convolution kernels configured to extract features from the individual patient data of the neural status and the therapeutic brain network response map.

In some examples, values in the convolution kernels are learned during a training of the statistical prediction model for the treatment.

In some examples, methods may include repeatedly multiplying each convolution kernel with the individual patient data and the therapeutic brain network response map, and storing results as pixels in a plurality of feature maps.

In some examples, the statistical prediction model may include a deep convolutional neural network comprises stacked convolution, rectified linear unit, and pooling layers configured to extract further features from the feature maps.

In some examples, methods may include predicting the efficacy based on the further features from the feature maps.

In some examples, methods may include predicting parameters for the treatment using the statistical prediction model.

In some examples, the treatment includes vagus nerve stimulation and the neural status may be a seizure.

In some examples, the individual patient data of the neural status comprises data of epileptiform spike or seizure network image indicative of brain regions in a seizure generation and propagation and pathways between these regions.

In some examples, obtaining the individual patient data of the neural status comprises using an electroencephalogram (EEG) or magnetoencephalogram (MEG), and obtaining the therapeutic brain network response map comprises using functional magnetic resonance imaging (fMRI), positron emission tomography (PET), and/or single-photon emission computed tomography (SPECT).

In some examples, obtaining the individual patient data of the neural status includes using group averaged spikes and source localization, using spike ICA analysis and source localization, using seizure network analysis, or combinations thereof.

In some examples, obtaining the individual patient data includes projecting data onto a brain space, identifying brain regions that are involved in the neural status, calculating pathways between seizure brain regions, or combinations thereof.

In some examples, the therapeutic brain network response map corresponds to a brain response to the treatment using a certain set of parameters.

Examples of systems are described herein. An example system may include at least one processor, and computer readable media encoded with instructions that, when executed by the at least one processor, cause the system to provide image data of a neural status of a patient and a therapeutic brain network response map as inputs to a statistical prediction model for a treatment, and predict an efficacy of the treatment using the statistical prediction model.

In some examples, the statistical prediction model may include convolution kernels configured to extract features from the individual patient data of the neural status and the therapeutic brain network response map.

In some examples, values in the convolution kernels are learned during a training of the statistical prediction model for the treatment.

In some examples, the instructions may further cause the system to repeatedly multiply each convolution kernel with the individual patient data and the therapeutic brain network response map, and store results as pixels in a plurality of feature maps.

In some examples, the statistical prediction model may include a deep convolutional neural network comprises stacked convolution, rectified linear, and pool layers configured to extract further features from the feature maps.

In some examples, the instructions may further cause the system to predict the efficacy based on the further features from the feature maps.

In some examples, the instructions may further cause the system to predict parameters for the treatment using the statistical prediction model.

In some examples, the treatment may include vagus nerve stimulation and the neural status may be a seizure.

In some examples, data of the neural status comprises data of an epilepsy source image indicative of a seizure origin.

In some examples, systems may include an electroencephalogram (EEG) system coupled to the at least one processor or a magnetoencephalogram (MEG) system coupled to the at least one processor and configured to provide the image data, and a functional magnetic resonance imaging (MRI) system coupled to the at least one processor and configured to provide the therapeutic brain network map.

DETAILED DESCRIPTION

Figure 1:
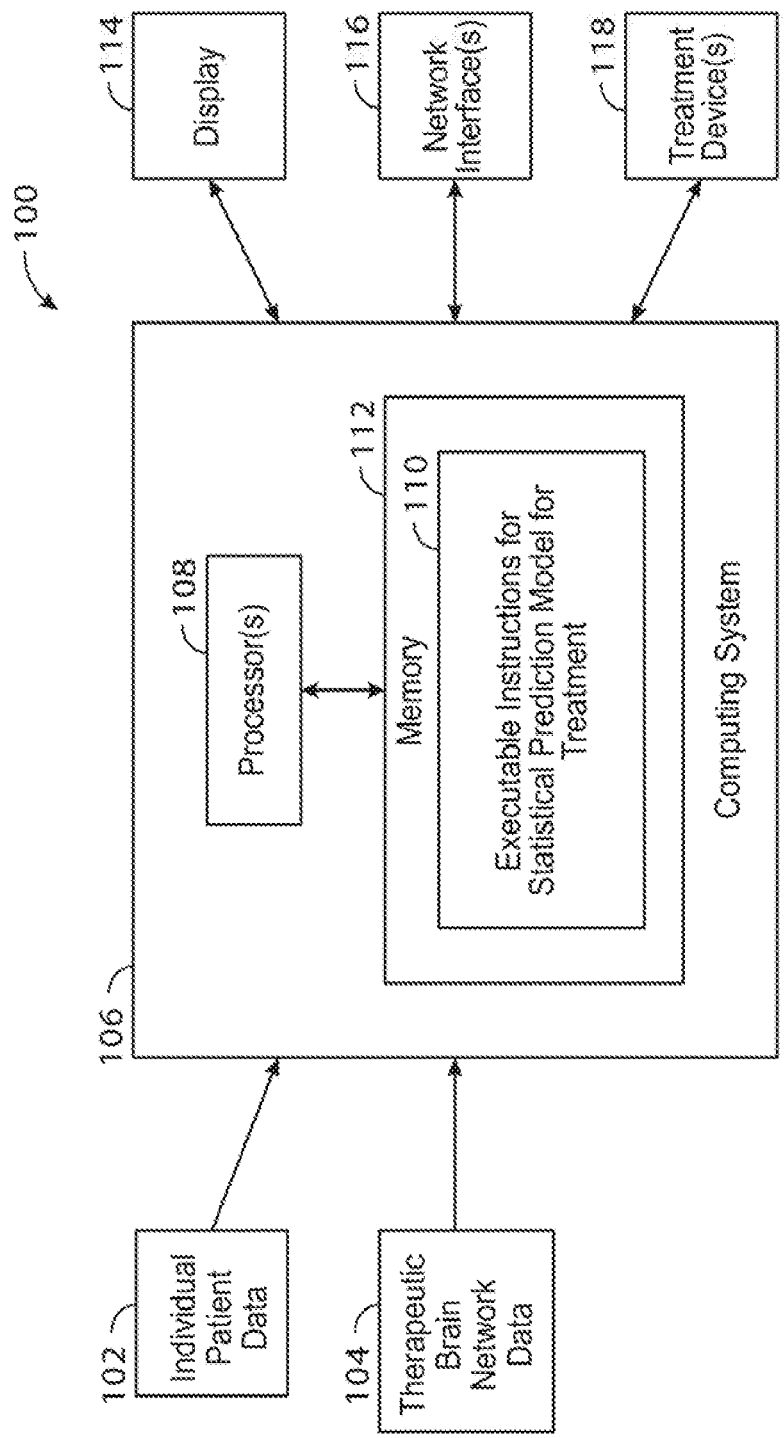
FIG. 1 is a schematic illustration of a system arranged in accordance with examples described herein.

Certain details are set forth below to provide a sufficient understanding of described embodiments. However, it will be clear to one skilled in the art that embodiments may be practiced without these particular details. In some instances, well-known brain imaging techniques and systems, circuits, control signals, timing protocols, and/or software operations have not been Shown in detail in order to avoid unnecessarily obscuring the described embodiments.

Examples of systems and methods described herein may predict the efficacy of a treatment (e.g., neurostimulation, drugs, cell therapy, gene therapy), which may aid in avoiding unnecessary treatment (e.g., neurostimulation implant surgery). Examples of systems and methods described herein may predict the most effective treatment parameters (e.g., stimulation parameters) for each individual patient before or after surgery to avoid long tedious stimulation parameter adjustment process.

Examples described herein may utilize a statistical prediction model, which may be based on brain source imaging and/or brain network analysis. Brain source imaging, such as imaging using source localized electroencephalogram (EEG) and magnetoencephalogram (MEG) may be utilized instead of the scalp recorded electric potential time series so that the recorded brain activity can be estimated on or inside the brain instead of on the scalp in some examples. Brain network analysis may also be utilized so that the brain regions involved in the neurological disease and the pathways between these regions can be estimated. In some examples, brain network response maps induced by a treatment (e.g., neurostimulator) are also acquired for the prediction, which contains information of the neurostimulation mechanisms and can further improve the prediction accuracy. The therapeutic brain network response map can be acquired by techniques such as, but not limited to, whole brain imaging techniques such as the functional magnetic resonance imaging (fMRI), positron emission tomography (PET), and/or single-photon emission computed tomography (SPECT).

Examples described herein may provide efficacy and/or parameter prediction services. One or more patient's EEG recordings may be received. Epileptiform spike(s) and/or seizure network(s) for the patients may be analyzed and a statistical prediction model may be applied to predict a treatment efficacy based on features that compare the disease state images (e.g., epileptiform spike(s) or seizure network image(s)) and representative fMRI brain network response maps for a therapy. The predicted efficacy and suggested parameters may then be provided. With this service, long neurostimulation parameter adjustment processes for therapies can be eliminated and/or reduced, success rate of therapy can be improved, and unnecessary implantations or other interventions may be avoided.

Examples described herein may go beyond simply predicting with epilepsy Types or spikes sources, rather, both EEG disease state image and fMRI brain network response maps may be utilized by the statistical prediction model, where the disease state image (e.g. spike and/or seizure network image(s)) may be indicative of the cause and/or evolution of a patient disease status (e.g. a seizure), and the fMRI maps may be indicative of the therapeutic activities induced by the therapy (e.g., vagus nerve stimulation (VNS)). By comparing the two, how VNS affects the seizure generation and/or propagation may be analyzed and the prediction accuracy may be significantly improved. In some examples, a deep neural network may be applied to autonomously learn optimal features from the disease state image (e.g., EEG spike(s) and/or seizure network image(s)) and the fMRI brain network response maps. While simple features such as a pixel-wise comparison between the EEG and fMRI maps can be utilized, weighting brain regions differently in EEG and fMRI maps may also be utilized for accurate prediction. DNN offers an opportunity to extract features autonomously, which may be more optimal than manually designed features. In some examples, only clinical routine status data (e.g., epilepsy EEG recordings) may be needed from the patients for the therapy (e.g., VNS) efficacy prediction, which may save the patients from additional examinations. Generally, many patients without dramatic brain damage may share similar brain network response to therapy and the therapeutic brain network response maps can also be fixed in the model.

Examples described herein may utilize comparisons of patient brain status data and brain network maps of treatments to predict efficacy of a treatment and/or predict parameters for use in the treatment of a neurological condition. In some examples, statistical prediction models are used to perform the comparison and/or prediction. The comparisons and statistical prediction models described herein may be implemented in hardware, software, or combinations thereof. For example, software may be used to implement a comparison and/or a statistical prediction model. The software may be programmed on one or more computing systems. For example, one or more processors may be coupled to computer readable media, which may encode executable instructions for one or more statistical prediction models for treatments.

FIG. 1 is a schematic illustration of a system arranged in accordance with examples described herein. The system 100 includes individual patient data 102, therapeutic brain network map 104, computing system 106, processor(s) 108, executable instructions for statistical prediction model for treatment 110, memory 112, display 114, network interface(s) 116, and treatment device(s) 118. Additional, fewer, and/or other components may be used in other examples.

Examples described herein may utilize data of a patient's neural status (e.g., image data relating to a neurological event), such as individual patient data 102 of FIG. 1. Individual patient data relating to any of a variety of neural events may be used, including, but not limited to, a seizure (e.g., an epileptic seizure), Parkinson's condition, Alzheimer's condition, or depression. For example, the individual patient data may be associated with an epileptiform spike source image illustrating the origin of a seizure and/or a seizure network image illustrating brain regions involved in a seizure and pathways between these regions (e.g., sequence of the seizure activity). The individual patient data may be obtained, for example, using source localization and/or brain network analysis of electroencephalogram (EEG) and/or magnetoencephalogram (MEG). Generally, EEG refers to a functional neuroimaging method that detects brain electrical activities using non-invasive or invasive electrodes. Generally. MEG refers to a functional neuroimaging method that Measures electromagnetic field changes around the brain to map brain activities. Source localization images generally refer to the use of multiple brain electrical signals measured outside of brain to identify the electrical activity on and/or inside the brain. Brain network analysis generally refers to the use of mathematical and statistical algorithms to identify brain regions involved in the brain electrical activity (such as a seizure) and the pathways among these regions (such as the sequence of seizure activity).

The individual patient data may correspond to a 1-dimensional time series, 2-dimensional or 3-dimensional image. In some examples, one set of individual patient data 102 may be used, e.g., corresponding to an image of a brain undergoing a neural event. In some examples, multiple sets of individual patient data 102 may be used, e.g., corresponding to multiple images of the brain undergoing several neural events. Generally, the individual patient data 102 used may be from the patient to be treated.

Figure 5:
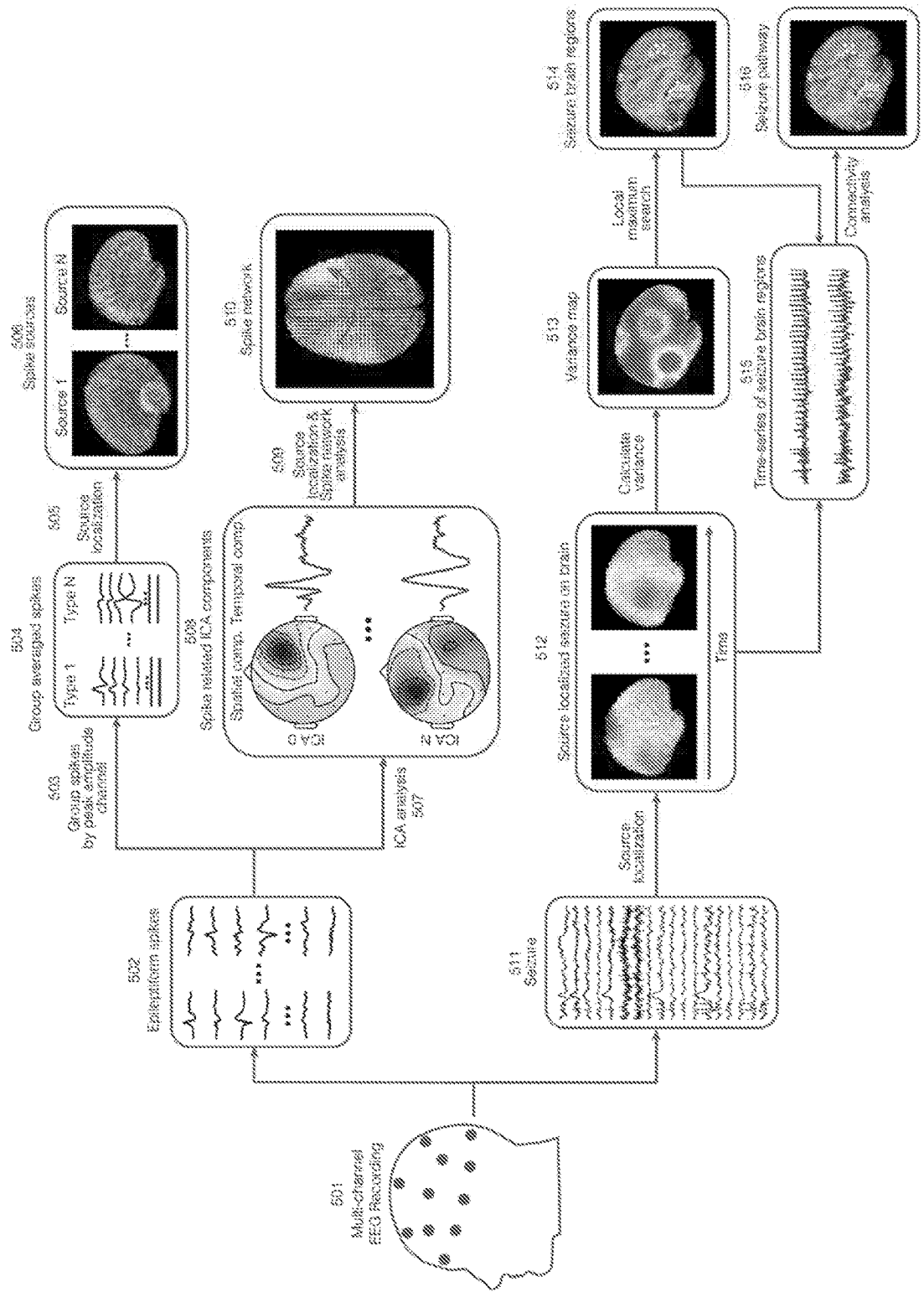
FIG. 5 is a schematic illustration of epileptiform spike or seizure network analysis in accordance with examples described herein.

An example of generating individual patient data 102 using EEG epileptiform spikes will now be described with reference to FIG. 1 and FIG. 5. FIG. 5 is a schematic illustration of epileptiform spike or seizure network analysis in accordance with examples described herein. The process and data shown in FIG. 5 may be collected and/or manipulated by the system of FIG. 1 in some examples. EEG generally refers to a method that is used to record brain electrical activities from the scalp. It is may be used in epilepsy diagnosis, for example, to detect epileptiform spikes and seizures. During an epilepsy EEG monitoring session, brain signals of an epilepsy patient may be continuously monitored using multiple electrodes. FIG. 5 includes a schematic illustration of a patient fitted with electrodes for a multi-channel EEG recording, EEG 501. Generally any number or placement of electrodes may be used. The EEG recording may generate data, such as epileptiform spikes 502 and/or seizure data 511 shown in FIG. 5. Other or different EEG data may also be generated in some examples. Abnormal epileptiform spikes 502 may be marked, for example, by professional EEG readers. These epileptiform spikes 502 may be related to the seizure generation and the source of these spikes may indicate abnormal brain regions. In the epilepsy EEG analysis, a scalp potential map at the peak (or other locations) of an epileptiform spike may be first computed. Then, based on an inverse electrical brain signal propagation model, the source of the spike on or inside the brain can be identified. Multiple EEG source localization algorithms may be used, such as linear distributed algorithms including minimum norm least squares (MNLS), dynamic statistical parametric mapping (dSPM), low-resolution brain electromagnetic tomography (LORETA), standardized LORETA (sLORETA), exact LORETA (eLORETA), etc., and dipole source localization algorithms such as non-linear least square, beamforming, multiple signal classification (MUSIC), etc.

In one example, a raw EEG recording may be first filtered with a bandpass filter (e.g., a 0.1 to 70 Hz bandpass filter) and a notch filter (e.g., a 60 Hz notch filter) to remove unwanted noise. The simultaneous EKG recording may then be analyzed to help identify cardiac artifacts in the EEG recordings. The cardiac artifacts may then be eliminated and/or reduced using algorithms such as the Signal-Space Projection (SSP) or Independent Component Analysis (ICA). After the preprocessing, epileptiform spikes may be identified manually by a professional EEG reader or automatically using software (e.g. Persyst P13, BESA epilepsy) from the EEG recording. In some examples, a professional EEG reader may then review and verily the software detected spike selection.

Two different types of spike source localization analyses may be applied to the selected spikes for each patient. For the first analysis, individual spikes are categorized by the EEG channel that has the largest amplitude at the spike peak, as shown by operation 503 in FIG. 5. For example, if certain spike shows the highest amplitude at T3 channel, it is marked as a T3 spike. Other categorization methods may additionally or instead be used. Spikes within each category may then be averaged, to provide averaged spikes 504. Source localization analysis 505 may be performed for the averaged spikes 504. One or multiple averaged spike sources 506 can then be identified and may be used as all or part of individual patient data 102. The spike sources generally refer to an identification of one or more regions of a brain and/or brain network which may contribute to the cause of one or more seizures. The executable instructions 110 of FIG. 1 may include executable instructions for performing categorization (e.g., operation 503 of FIG. 5) and/or source localization (e.g., operation 505 of FIG. 5).

Instead of or in addition to averaging spikes, in a second analysis, independent component analysis (ICA) may be applied to identify independent spike sources. ICA is shown as operation 507 in FIG. 5. Spikes identified for each subject may be first analyzed using spatial ICA. Multiple ICA components 508 may include spatial and temporal subcomponents which may be identified, where each may represent a possible independent spike electrical potential map. The ICA weight across time may then be visualized (e.g., displayed, such as by using display 114 of FIG. 1) to verify if the corresponding ICA map is originated from spike or noise. For example, ICA component 0 and 1 may show a high peak during the spike discharge for most of the spike epochs, while ICA component 2's weight changing across time shows a noisy pattern. Therefore, only ICA component 0 and 1 are independent spike sources, while ICA component 2 is noise. After the ICA analysis. ICA spatial maps may then be fed into the source localization algorithm, shown as operation 509 in FIG. 5, to identify the corresponding spike network 510. Such spike network 510 data may be used as all or part of individual patient data 102 of FIG. 1. The executable instructions 110 of FIG. 1 may include executable instructions for performing ICA analysis (e.g., operation 507 of FIG. 5) and/or source localization and spike network analysis (e.g., operation 510 of FIG. 5).

In some examples, alternatively or additionally, seizure network analysis may be used for generating individual patient data using EEG, such as individual patient data 102 of FIG. 1. EEG recordings from the multi-channel EEG recording 501 are shown as seizure EEG 511 of FIG. 5. One or multiple episodes of seizure in the seizure EEG 511 may be annotated either manually and/or by a professional EEG reader or automatically by software (e.g. Persyst P13, BESA epilepsy). Episode(s) of seizure within a long seizure EEG may be extracted and preprocessed analogous to that shown and described with respect to methods using ICAs, e.g., bandpass filtering, notch filtering, noise and/or artifact suppression may be used. The preprocessed seizure EEG 511 may be source localized onto the brain using source localization methods analogous to those described with respect to methods using group averages and/or ICAs. A sequence of source localized seizure data 512 in the brain space can be provided. The source localized seizure data may include an association, over time, between particular brain regions and brain activity (e.g., seizure activity).

Seizure network analysis may be performed with one or multiple of the source localized seizure data 512 (e.g., one or more collections of data representing all or portions of a brain at a particular time). During the analysis, brain regions that the seizure started at and propagated to may be identified. This identification algorithm may first calculate the variance across the time for brain voxels in the source localized space, then search for local variance maximums across brain voxels to provide a variance map 513. The variance map 513 may provide the brain signal variance at particular brain locations and/or regions. Brain regions involved during the seizure, e.g., seizure brain regions 514 can be computed as regions that are local maximums in the variance map 513. For example, regions having a greatest variance across the neighboring brain regions may be determined to be the center of the seizure brain regions.

In a more generalized scenario, source localized seizure episodes may first be segmented into overlapping epochs (overlapping window analysis), and the same variance local maximum calculation can be performed to identify brain regions involved during each epoch of the seizure. Brain regions that are consistently involved across all seizure epochs can then be identified by averaging or statistical testing across all brain regions estimated from the segmented seizure epochs.

EEG source localized time-series data for each brain region identified as a seizure brain region may be extracted. For example, the time-series data of seizure brain regions 515 of FIG. 5 may be extracted by extracting data from the source localized seizure data 512 which corresponds to seizure brain regions 514. Accordingly, the time-series data of seizure brain regions 515 may correspond to EEG data associated with regions of the brain active during seizure. Pathways between these brain regions may be analyzed together with these time-series. For example, a connectivity analysis may be used to identify one or more seizure pathways, e.g., seizure pathway 516, which may indicate connections between brain regions which may be involved in producing, sustaining, and/or ending a seizure event. Seizure pathway analysis methods which may be used include correlation, coherence, imaginary coherence, phase locking value, auto-aggressive modeling, and/or partial directed coherence. Other analysis methods may also be used. The executable instructions 110 of FIG. 1 may include executable instructions for performing source localization (e.g., providing source localized seizure data 512 of FIG. 5) and/or variance calculation, maximum search, time-series extraction, and/or connectivity analysis (e.g., providing variance map 513 of FIG. 5, providing seizure brain regions 514 of FIG. 5, providing time-series of seizure brain regions 515 of FIG. 5, and/or providing seizure pathway 516 of FIG. 5). Seizure brain regions 514, seizure pathway 516, time-series of seizure brain regions 515, and/or other data shown or described with reference to FIG. 5 may be used as all or part of individual patient data 102 of FIG. 1.

Other metrics may be used additionally to or instead of spike source localization and seizure network analysis results include. Other metrics include, but are not limited to spike propagation network map, ICA-based seizure source localization map, which may also or instead be used as all or part of individual patient data 102.

Examples described herein may utilize one or more brain network response maps, such as therapeutic brain network map 104 of FIG. 1, Brain network response maps described herein may refer to image data of brain responses to a treatment utilizing a certain set of treatment parameters. The brain network response maps, such as therapeutic brain network map 104, may be obtained using functional magnetic resonance imaging (fMRI), positron emission tomography (PET), and/or single-photon emission computed tomography (SPECT). fMRI generally refers to a method that indirectly measures brain activities by using blood oxygen level changes. The therapeutic brain network response maps may be 2-dimensional or 3-dimensional, and in some examples may be aligned to the individual patient data 102 (e.g., aligned to an epilepsy spike or seizure network image). Any number of therapeutic brain network maps may be used. Generally, multiple brain network maps may be used which correspond to different sets of parameters for the treatment (e.g., one set of parameters may be used to generate one brain network map, and another set of parameters may be used to generate another brain network map). In some examples, one or more of the brain network maps, such as therapeutic brain network map 104 may be from the patient (e.g., a same patient as associated with the individual patient data 102). However, in some examples, one or more of the brain network maps may be wholly and/or partially derived from data from other patients other than the patient being treated (e.g., other than the patient from whose brain activity the individual patient data 102 is derived). In some examples, one or more brain network maps represent an average or other combination of maps from a group of patients or maps measured for a specific patient. For example, one of the brain network maps may be a brain network map that is a combination (e.g. average) of multiple brain network maps from different patients using same therapeutic parameters (e.g., frequency, amplitude, duration). In some examples utilizing neurostimulation therapy, if a patient has not been implanted, then brain network maps or combinations of brain network maps from other patients may be used. If a patient has been implanted, brain network maps associated with the patient may be used, or may be used in combination with other brain network maps. The brain network response maps, such as therapeutic brain network map 104, generally illustrate areas of brains affected by a treatment.

An example of fMRI used to obtain a therapeutic brain network map may now be described. Generally, functional magnetic resonance imaging is a method that enables whole brain activity monitoring using blood oxygen level changes. fMRI may be utilized herein record the therapeutic brain activities induced by one or more therapies, such as neurostimulations vagus nerve stimulation). In a patient with a neurostimulator, the neurostimulator may be programmed to one of the parameter settings under-investigation and the patient may then be scanned using an MRI scanner. During the image pre-processing, fMRI is motion corrected and aligned to a standard template brain. Brain activities that are related to the designed therapy (e.g., neurostimulation) will then be statistically analyzed using the general linear model (GLM) or other equivalent fMRI analysis method. Multiple subjects may be scanned and the average response of the targeting population group may be concluded and may be used as one or more of the brain network maps described herein, such as therapeutic brain network map 104.

In addition to or instead of an averaged fMRI map, other potential metrics may be used to quantify the therapeutic function of the therapy (e.g., neurostimulation). For example, these metrics include but not limited to quantifying the frequency of how often each region becomes active in fMRI during the neurostimulation, and the group t-test statistics map of the individual fMRI maps.

Brain network maps may generally be provided relating to any of a number of treatments including, but not limited to, neurostimulation therapies (e.g., vagus nerve stimulation (VNS), responsive neurostimulation (RNS), transcranial magnetic stimulation (TMS), and deep brain stimulation (DBS)), pharmaceutical therapies, and/or talk or experiential therapies. Generally, neurostimulation may refer to therapy for treating neurological and psychiatric diseases. Electrical stimulation may be utilized its neurostimulation therapy to directly or indirectly activate or inhibit brain networks. In some examples, brain network maps may be provided associated with a particular set of parameters of the stimulation (e.g. for a certain stimulation frequency and amplitude for neurostimulation, or for a certain dosage and frequency of pharmaceutical therapy). Vagus nerve stimulation (VNS) generally refers to one type of neurostimulation. In VNS, a stimulator is implanted under skin and sends electrical pulses through the left vagus nerve. VNS may be used for drug resistant epilepsy, depression, and many other neurological and psychiatric diseases. While some examples may be described herein with reference to VNS, it is to be understood other therapies may additionally or instead be used.

The individual patient data 102 and/or therapeutic brain network map 104 may be stored in a memory accessible to the computing system 106 and/or transmitted to the computing system 106 (e.g., using wired or wireless communication). The computing system 106 may be configured to predict an efficacy of a treatment and/or parameters for use in a treatment based on a comparison and/or statistical prediction model for the treatment.

Examples described herein may utilize computing systems, which may generally include hardware and/or software for implementing comparisons and/or statistical prediction models for treatments. For example, the computing system 106 may include one or more processor(s) 108. The processor(s) 108 may be implemented, for example, using one or more central processing units (CPUs), graphical processing units (GPUs), application-specific integrated circuits (ASICs), field programmable gate arrays (FPGA), or other processor circuitry. The processor(s) 108 may be in communication with memory 112. The memory 112 may generally be implemented by any computer readable media (e.g., read-only memory (ROM), random access memory (RAM), flash, solid state drive, etc.). While a single memory 112 is shown, any number may be used, and they may be integrated with the processor(s) 108 in a single computing system 106 and/or located within another computing system and in communication with processor(s) 108.

The memory 112 may be encoded with executable instructions for a comparison of the individual patient data 102 with the therapeutic brain network map 104. Examples of comparisons described herein include evaluating an overlap between the brain activity evidenced by the individual patient data 102 and the areas of the brain affected by the treatment at the parameters used to generate the therapeutic brain network map 104. Generally, for many treatments, overlap of the areas of the brain affected as shown in the individual patient data 102 and areas of the brain accessed by treatment as shown in therapeutic brain network map 104, may indicate that the treatment at the parameters used for therapeutic brain network map 104 may be effective in treating the patient having the individual patient data 102.

In some examples, the executable instructions for comparison may include executable instructions for statistical prediction model for treatment 110. In some examples, the executable instructions for statistical prediction model for treatment 110 includes instructions for implementing deep artificial neural network with convolution kernels configured to extract features from image data (e.g. Individual patient data 102) of the neural status and one or more brain network response maps (e.g., therapeutic brain network map 104). Values in the convolution kernels may in some examples be learned during a training of the statistical prediction model for the treatment.

The executable instructions for statistical prediction model for treatment 110 may include instructions for repeatedly multiplying each convolution kernel with the individual patient image data and the therapeutic brain network response map, and storing results as pixels in a plurality of feature maps. The statistical prediction model may include a deep convolutional neural network comprises stacked convolution, rectified linear, and pooling layers configured to extract further features from the feature maps. The executable instructions for statistical prediction model for treatment 110 may include instructions for predicting the efficacy of the treatment based on the further features from the feature maps.

In some examples, the executable instructions for statistical prediction model for treatment 110 may include instructions for predicting parameters for the treatment using the statistical prediction model. For example, therapeutic brain network maps input into computing system 106 may include brain network maps relevant to use of the treatment at different parameters. The statistical prediction model may accordingly recommend parameters for the treatment (e.g., amplitude, frequency, duration, dosage, etc.). The output of the computing system operating in accordance with the executable instructions for statistical prediction model for treatment 110 may be a treatment efficacy and/or recommended parameters. For example, where the statistical prediction model predicts the treatment will be effective, recommended parameters may be output. If the statistical prediction model predicts the treatment will not be effective, then "not effective" may be reported. Note that multiple individual patients may be evaluated using the statistical prediction model. In this manner, computing system 106 may facilitate faster and more accurate predictions of treatment efficacy and parameters settings across patient populations than possible using previous systems or with unaided physician evaluation of patient records.

In some examples, the system 100 may include display 114, which may be in communication with computing system 106 (e.g., using a wired and/or wireless connection), or the display 114 may be integrated with the computing system 106. The display 114 may display a predicted efficacy of a treatment and/or recommended parameters for a treatment based on the comparison and/or statistical model implemented by the computing system 106. Any number or variety of displays may be present, including one or more LED, LCD, plasma, or other display devices.

In some examples, the system 100 may include network interface(s) 116. The network interface(s) 116 may provide a communication interface to any network (e.g., LAN, WAN, Internet). The network interface(s) 116 may be implemented using a wired and/or wireless interface (e.g., Wi-Fi, BlueTooth, HDMI, USB, etc.). The network interface(s) 116 may communicate data regarding the predicted efficacy of a treatment and/or recommended parameters for a treatment based on the comparison and/or statistical model implemented by the computing system 106.

In some examples, the system 100 may include one or more treatment device(s) 118. The treatment device(s) 118 may be implemented using, for example, systems capable of neurostimulation (e.g., vagus nerve stimulation systems). The treatment device(s) 118 may be implemented using, for example, systems capable of administering pharmaceutical treatment (e.g., injection devices, pill dispensers, etc.). The treatment device(s) 118 may be programmed or otherwise configured to implement a treatment and/or utilize treatment parameters recommended by the computing system 106. The treatment device(s) 118 may communicate with computing system 106 in some examples using network interface(s) 116.

Figure 2:
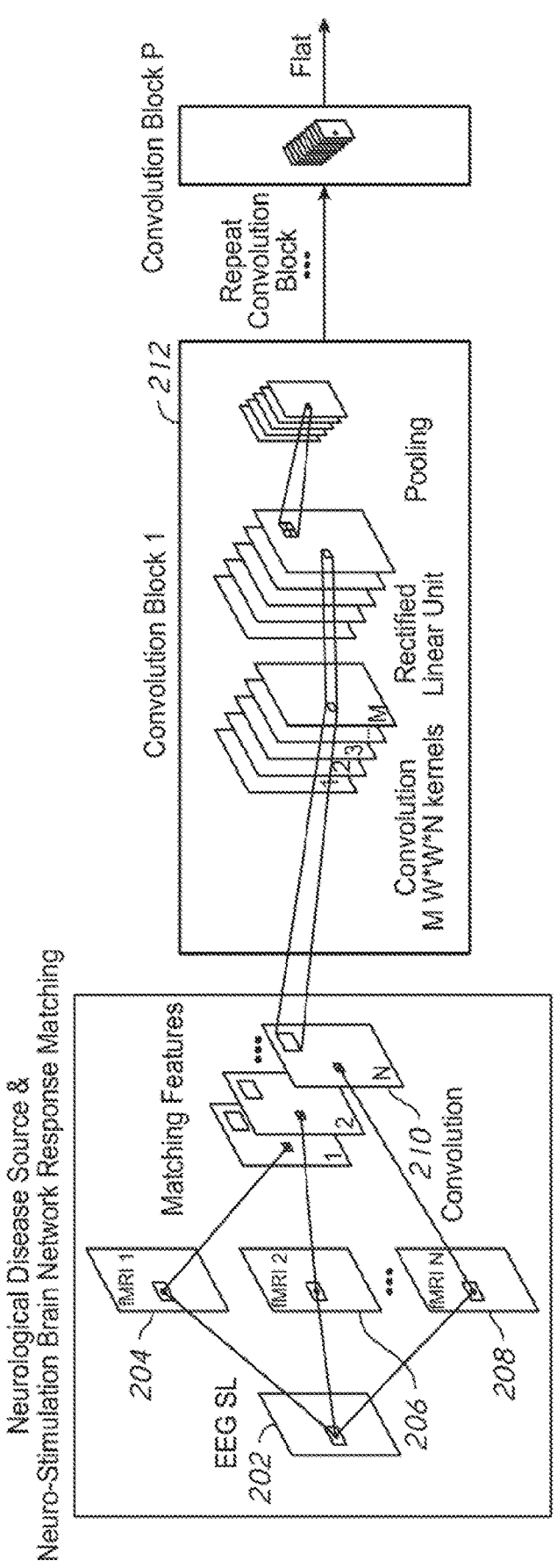
FIG. 2 illustrates a statistical prediction model process 200 in accordance with examples described herein.

FIG. 2 illustrates a statistical prediction model process 200 in accordance with examples described herein. The statistical prediction model process 200 includes individual patient data 202, therapeutic brain network map 204, therapeutic brain network map 206, therapeutic brain network map 208, feature map 210, and convolution, rectified linear unit, and pooling layers 212. The executable instructions for statistical prediction model for treatment 110 of FIG. 1 may be used in some examples to implement the statistical prediction model process 200 shown in FIG. 2.

As shown, individual patient data 202 (which may be implemented by and/or used to implement individual patient data 102 of FIG. 1) is provided as an input. As discussed herein, the individual patient data may generally be related to an image of a patient brain status. The individual patient data may, for example, illustrate a brain region where seizure originates from, regions where seizure propagates or other neural event. The individual patient data 202 may be data relating to an EEG spike or seizure network image. A number of brain network maps may also be provided as input, such as therapeutic brain network map 204, therapeutic brain network map 206, and therapeutic brain network map 208 of FIG. 2. The brain network maps of FIG. 2 may be used to implement and/or may be implemented by therapeutic brain network map 104 of FIG. 1 in some examples. The brain network maps may each represent the effect of a particular therapy (e.g., neurostimulation) at different parameter values (e.g., frequency, amplitude, duration). The individual patient data 202 and therapeutic brain network maps may be compared. For example, a group of convolution kernels may be used to compare the individual patient data 202 and therapeutic brain network maps, resulting, in feature map 210. Parameters of the kernels may be learned during training of the statistical prediction model. The convolution kernels are used to automatically extract features between the individual patient data (e.g., epilepsy source image) and the therapeutic brain network response maps. Each convolution kernel may be repeatedly multiplied with the input data and/or therapeutic brain network maps to compare the two and the results may be stored as pixels in multiple feature maps, such as feature map 210.

Next, a deep convolutional neural network may be used to further analyze the comparison (e.g., further analyze feature map 210). Deep neural networks generally refer to a type of artificial neural network statistical model that may have ten to hundreds of layers for highly complex artificial intelligent tasks. In other examples, other models may be used. The deep convolutional neural network may utilize multiple convolution blocks, with each convolution block including multiple possible operations such as multi-kernel convolution, rectified linear unit, and (max/average) pooling, as shown by convolution, RLU, and pooling layers 212. The order of theses layers does not necessarily need to follow this order. These layers are designed to further extract features from feature maps previously generated. Multiple convolution blocks may be utilized until a final convolution block—"convolution block. P" of FIG. 2—is obtained.

Figure 3:
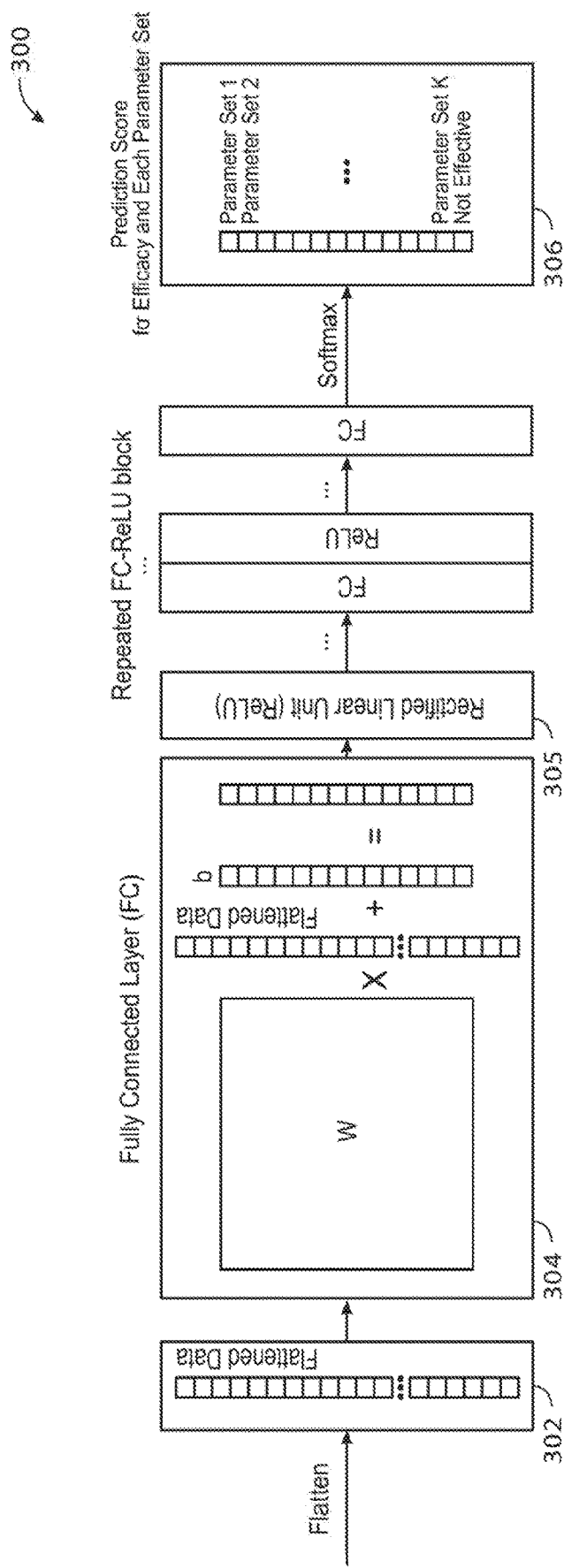
FIG. 3 illustrates a statistical prediction model process 300 in accordance with examples described herein.

FIG. 3 illustrates a statistical prediction model process 300 in accordance with examples described herein. FIG. 3 may receive an input from the process of FIG. 2—e.g., from a final convolution block of a neural network. FIG. 3 illustrates flattened data 302, fully connected layer 304, rectified linear unit 305, and prediction score(s) 306. There may be multiple blocks of the fully connected and rectified linear unit layers 304 and 305. The executable instructions for statistical prediction model for treatment 110 may be used to implement all or portions of the statistical prediction model process 300 of FIG. 3.

The flattened data 302 may be generated by flattening an output of the final convolution block of FIG. 2 The fully connected layer 304 may be used to shrink a number of features to the number of prediction categories. For example, each treatment may have a set of different possible parameter values for use. Each parameter set may represent one prediction category, plus there may be a category for overall efficacy of the treatment. As shown in FIG. 3, parameter sets 1-K may be evaluated.

A softmax layer may be applied to normalize the output of the fully connected layer to [0, 1]. A score may be calculated for each parameter set to provide prediction score(s) 306. A parameter set that meets certain criteria (e.g., highest) may be taken as the output of the prediction.

Figure 4:
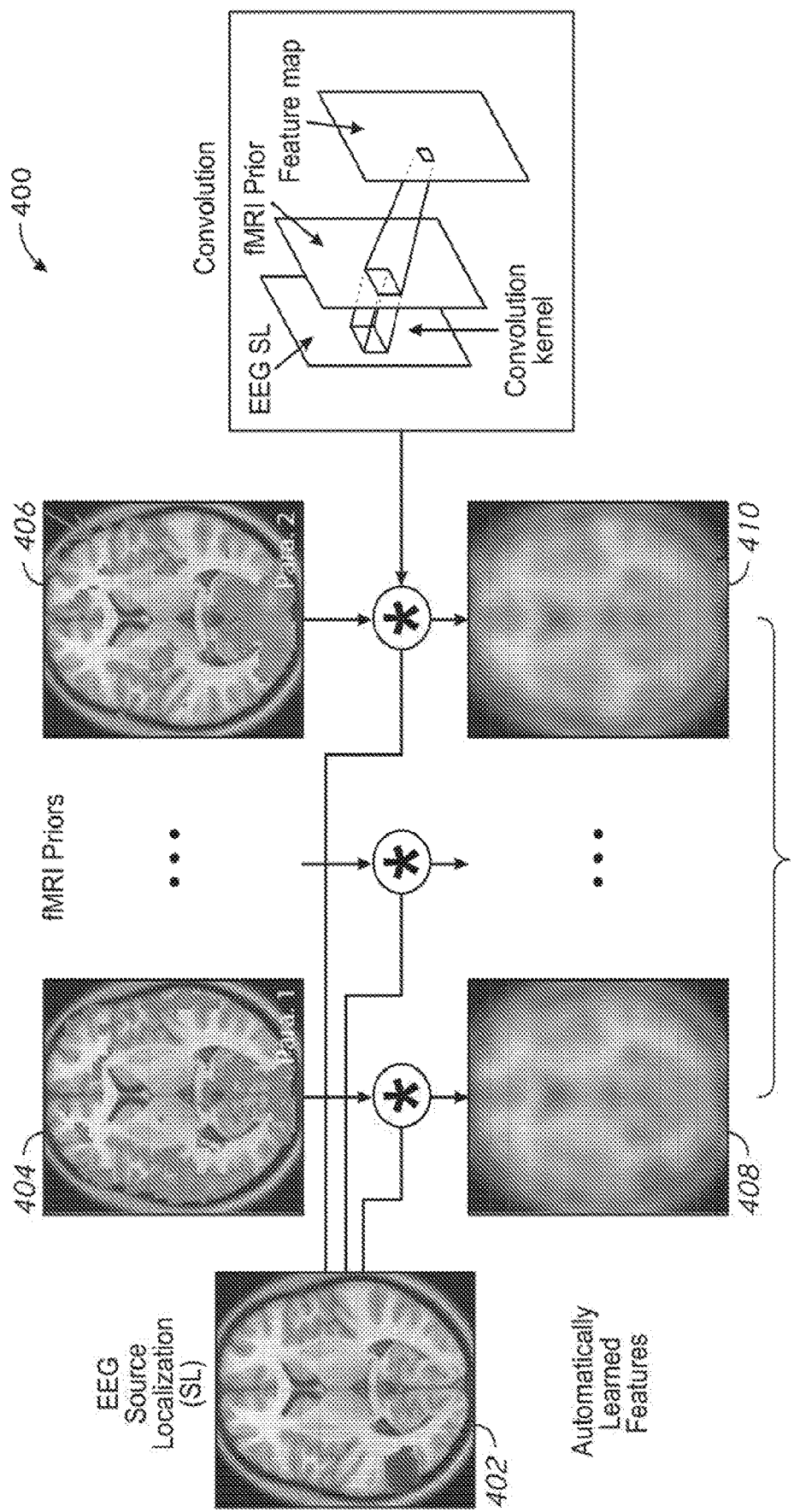
FIG. 4 illustrates an image set 400 in accordance with examples described herein.

FIG. 4 illustrates an image set 400 in accordance with examples described herein. Graphically, an image 402 associated with individual patient data is shown. The image 402 may, for example, be an EEG spike or seizure network image, which may depict a seizure origin and its propagated brain regions. Therapeutic brain network map 404 and therapeutic brain network map 406 may be MARI images from other patient(s) having a particular treatment at particular parameter levels. Convolution of these data sets may result in feature maps—feature map 408 and feature map 410, for example. The feature maps include information regarding a comparison of the individual patient data with therapeutic brain network maps.

In some examples, other machine learning techniques (e.g., non-deep neural network model) may also or instead be used to form a statistical prediction model to predict the efficacy and optimal parameters for therapies. Different from examples of the deep neural network model, features may be manually designed in some examples. Example features will be described that can be applied to predict the efficacy and optimal therapeutic parameters for the neurostimulation therapy, although other features may also be used. These features could also be learned in the deep neural network model when it compares the fMRI and EEG images.

Figure 6:
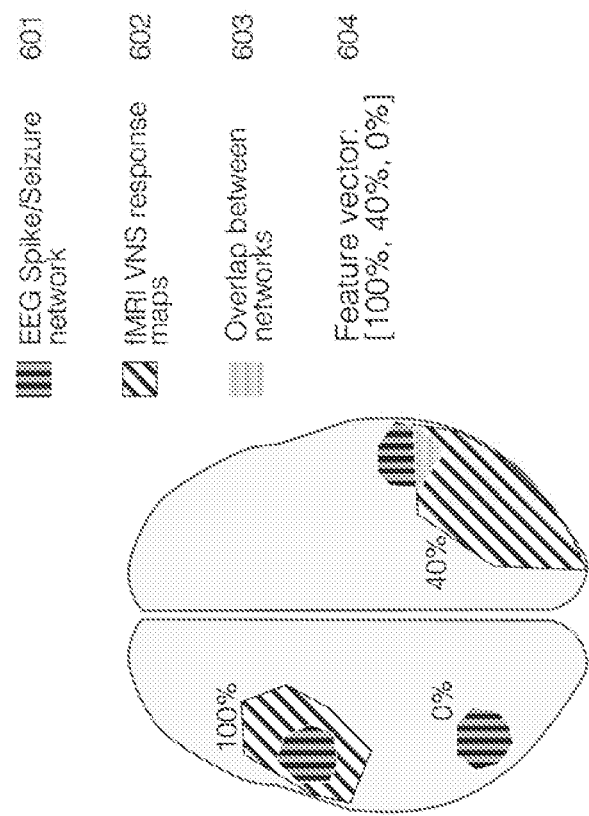
FIG. 6 illustrates a pixelwise feature extraction model for neurostimulation efficacy prediction arranged in accordance with examples described herein.

One such feature is the overlap area between the EEG spike or seizure network image and the fMRI activation images. FIG. 6 is a schematic illustration of brain regions arranged in accordance with examples described herein. The seizure network image is shown are regions 601. These regions, may for example, be seizure brain regions 514 of FIG. 5 and/or seizure pathway 516. The fMRI activation image is shown are regions 602. The regions 602 are those which are activated in a therapeutic brain network map described herein (which regions may or may not participate in the patient's seizure regions identified herein). The overlap area, shown are regions 603 in FIG. 6, between the EEG spike or seizure network image 601 (e.g., individual patient data 102) and the fMRI activation image 602 (e.g., therapeutic brain network map 104) can be utilized as a feature vector 604 in a statistical prediction model to determine whether the stimulator works better with a particular parameter (e.g., 20 or 30 Hz stimulation). For example, there is an area on the upper left of FIG. 6, where the seizure network 601 is fully contained within an active region of the fMRI activation images 602. Accordingly, that region may be indicated as 100%. There is an area on the lower right where there is a 40% overlap between the seizure network and the fMRI activation images. There is a further area on the lower left where there is a 0% overlap between the seizure network 601 and the fMRI activation images. Accordingly, the feature vector 604 may be given as [100%, 40%, 0%]. In one example, if the EEG spike or seizure network image has a larger overlap with the 20 Hz fMRI activation image than the 30 Hz, the 20 Hz neurostimulation may be predicted as preferred than the 30 Hz stimulation for this patient.

In general, the overlap area feature can be calculated between any individual patient data 102 and the therapeutic brain network map 104.

From the foregoing it will be appreciated that, although specific embodiments have been described herein for purposes of illustration, various modifications may be made while remaining with the scope of the claimed technology.

What is claimed is:

1. A method comprising:
obtaining individual patient data of a neural status of a patient;
obtaining a therapeutic brain network response map of a treatment; and
predicting an efficacy of the treatment for the patient based on a comparison of the data of the neural status and the brain network response map by:
providing the individual patient data and the therapeutic brain network response map as inputs to a statistical prediction model for the treatment, the statistical prediction model comprising convolution kernels configured to extract features from the individual patient data of the neural status and the therapeutic brain network response map; and
predicting the efficacy of the treatment using the statistical prediction model.

2. The method of claim 1, wherein the statistical prediction model comprises feature extraction techniques configured to extract features from the individual patient data regarding neural status and the brain network response map.

3. The method of claim 2, wherein the features comprise an overlap area between the individual patient data and the brain network response map.

4. The method of claim 1, wherein values in the convolution kernels are learned during a training of the statistical prediction model for the treatment.

5. The method of claim 1, further comprising repeatedly multiplying each convolution kernel with the individual patient data and the therapeutic brain network response map, and storing results as pixels in a plurality of feature maps.

6. The method of claim 5, wherein the statistical prediction model further comprises a deep convolutional neural network comprises stacked convolution, rectified linear unit, and pooling layers configured to extract further features from the feature maps.

7. The method of claim 6, further comprising predicting the efficacy based on the further features from the feature maps.

8. The method of claim 1, further comprising predicting parameters for the treatment using the statistical prediction model.

9. The method of claim 1, wherein the treatment comprises vagus nerve stimulation and the neural status comprises a seizure.

10. The method of claim 9, wherein the individual patient data of the neural status comprises data of epileptiform spike or seizure network image indicative of brain regions in a seizure generation and propagation and pathways between these regions.

11. The method of claim 1, wherein obtaining the individual patient data of the neural status comprises using an electroencephalogram (EEG) or magnetoencephalogram (MEG), and wherein obtaining the therapeutic brain network response map comprises using functional magnetic resonance imaging (fMRI), positron emission tomography (PET), and/or single-photon emission computed tomography (SPECT).

12. A method comprising:
obtaining individual patient data of a neural status of a patient using group averaged spikes and source localization, using spike ICA analysis and source localization, using seizure network analysis, or combinations thereof;
obtaining a therapeutic brain network response map of a treatment; and
predicting an efficacy of the treatment for the patient based on a comparison of the data of the neural status and the brain network response map.

13. The method of claim 12, wherein obtaining the individual patient data comprises projecting data onto a brain space, identifying brain regions that are involved in the neural status, calculating pathways between seizure brain regions, or combinations thereof.

14. The method of claim 1, wherein the therapeutic brain network response map corresponds to a brain response to the treatment using a certain set of parameters.

15. A system comprising:
at least one processor; and
non-transitory computer readable media encoded with instructions that, when executed by the at least one processor, cause the system to:
provide image data of a neural status of a patient and a therapeutic brain network response map as inputs to a statistical prediction model for a treatment, the statistical prediction model comprising convolution kernels configured to extract features from the individual patient data of the neural status and the therapeutic brain network response map; and predict an efficacy of the treatment using the statistical prediction model.

16. The system of claim 15, wherein values in the convolution kernels are learned during a training of the statistical prediction model for the treatment.

17. The system of claim 15, wherein the instructions further cause the system to repeatedly multiply each convolution kernel with the individual patient data and the therapeutic brain network response map, and store results as pixels in a plurality of feature maps.

18. The system of claim 17, wherein the statistical prediction model further comprises a deep convolutional neural network comprises stacked convolution, rectified linear, and pool layers configured to extract further features from the feature maps.

19. The system of claim 18, wherein the instructions further cause the system to predict the efficacy based on the further features from the feature maps.

20. The system of claim 15, wherein the instructions further cause the system to predict parameters for the treatment using the statistical prediction model.

21. The system of claim 15, wherein the treatment comprises vagus nerve stimulation and the neural status comprises a seizure.

22. The system of claim 21, wherein the data of the neural status comprises data of an epilepsy source image indicative of a seizure origin.

23. The system of claim 15, further comprising an electroencephalogram (EEG) system coupled to the at least one processor or a magnetoencephalogram (MEG) system coupled to the at least one processor and configured to provide the image data, and a functional magnetic resonance imaging (fMRI) system coupled to the at least one processor and configured to provide the therapeutic brain network map.

* * * * *